(12) United States Patent
Govari

(10) Patent No.: US 11,259,834 B2
(45) Date of Patent: Mar. 1, 2022

(54) BRAIN ANEURYSM TOOL WITH A WIRE DEFLECTION MECHANISM

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 112 days.

(21) Appl. No.: 16/662,445

(22) Filed: Oct. 24, 2019

(65) Prior Publication Data

US 2020/0129199 A1    Apr. 30, 2020

Related U.S. Application Data

(60) Provisional application No. 62/752,825, filed on Oct. 30, 2018.

(51) Int. Cl.
*A61B 17/3207*    (2006.01)
*A61B 5/06*    (2006.01)
(Continued)

(52) U.S. Cl.
CPC .......... *A61B 17/3207* (2013.01); *A61B 5/065* (2013.01); *A61B 17/1214* (2013.01); *A61B 17/12113* (2013.01); *A61B 6/032* (2013.01); *A61B 6/485* (2013.01); *A61B 2017/00022* (2013.01); *A61B 2017/00557* (2013.01);
(Continued)

(58) Field of Classification Search
CPC ........ A61B 17/12022; A61B 17/12113; A61B 17/1214; A61B 2017/1205; A61B 5/065
See application file for complete search history.

(56) References Cited

U.S. PATENT DOCUMENTS 5,108,407 A * 4/1992 Geremia .......... A61B 17/12022
604/57
5,725,534 A    3/1998 Rasmussen
(Continued)

FOREIGN PATENT DOCUMENTS

DE    102012104548    11/2013
GB    2469073    10/2010
(Continued)

OTHER PUBLICATIONS

European Search Report dated Mar. 30, 2020 from corresponding European Patent Application No. 19205962.4.
(Continued)

*Primary Examiner* — Ryan J. Severson
(74) *Attorney, Agent, or Firm* — Frost Brown Todd LLC

(57) ABSTRACT

A medical device for treating an aneurysm in a blood vessel includes a hollow shaft for insertion into the blood vessel, an exit port at a distal end of the shaft, a deflection element, and a position sensor. The hollow shaft encompasses a wire-insertion channel for leading a wire to be inserted into the aneurysm. The exit port is configured for exiting the wire from the wire-insertion channel and into the aneurysm. The deflection element is located adjacent to the exit port and configured to deflect the wire from the wire-insertion channel to the exit port. The position sensor, which is coupled to the distal end of the shaft, is configured to produce signals indicative of a position and orientation of the exit port in the blood vessel.

20 Claims, 3 Drawing Sheets

(51) Int. Cl.
*A61B 17/12* (2006.01)
*A61B 6/03* (2006.01)
*A61B 6/00* (2006.01)
*A61B 17/00* (2006.01)

(52) U.S. Cl.
CPC ............... *A61B 2017/1205* (2013.01); *A61B 2017/320733* (2013.01)

(56) References Cited

U.S. PATENT DOCUMENTS

| | | | |
|---|---|---|---|
| 5,980,554 A | 11/1999 | Lenker et al. | |
| 6,136,015 A * | 10/2000 | Kurz | A61B 17/12022 606/191 |
| 6,190,353 B1 * | 2/2001 | Makower | A61B 1/3137 604/95.01 |
| 6,302,875 B1 * | 10/2001 | Makower | A61B 8/12 604/528 |
| 6,463,317 B1 | 10/2002 | Kucharczyk et al. | |
| 6,616,617 B1 | 9/2003 | Ferrera et al. | |
| 6,655,386 B1 * | 12/2003 | Makower | A61B 1/3137 128/898 |
| 6,773,402 B2 * | 8/2004 | Govari | A61B 5/287 600/459 |
| 7,059,330 B1 * | 6/2006 | Makower | A61B 1/3137 128/898 |
| 7,918,793 B2 * | 4/2011 | Altmann | A61B 8/4488 600/437 |
| 7,966,057 B2 * | 6/2011 | Macaulay | A61B 8/5238 600/424 |
| 8,214,015 B2 * | 7/2012 | Macaulay | A61B 5/6852 600/424 |
| 9,277,923 B2 * | 3/2016 | Rangi | A61B 17/12113 |
| 9,579,104 B2 | 2/2017 | Beckham et al. | |
| 2001/0047165 A1 * | 11/2001 | Makower | A61B 17/12045 604/528 |
| 2004/0059280 A1 * | 3/2004 | Makower | A61B 17/12131 604/8 |
| 2004/0147837 A1 | 7/2004 | Macaulay et al. | |
| 2004/0176784 A1 * | 9/2004 | Okada | A61B 17/1285 606/142 |
| 2005/0020908 A1 | 1/2005 | Birkenbach | |
| 2010/0094259 A1 * | 4/2010 | Makower | A61B 17/12022 604/528 |
| 2012/0116352 A1 * | 5/2012 | Rangi | A61B 17/12045 604/509 |
| 2014/0236207 A1 * | 8/2014 | Makower | A61B 17/12136 606/185 |
| 2016/0120551 A1 | 5/2016 | Connor | |
| 2020/0129199 A1 * | 4/2020 | Govari | A61B 5/6822 |

FOREIGN PATENT DOCUMENTS

| | | |
|---|---|---|
| WO | WO 1997/013463 | 4/1997 |
| WO | WO 1998/046119 | 10/1998 |
| WO | WO 2018/045156 | 3/2018 |

OTHER PUBLICATIONS

U.S. Appl. No. 62/675,952, filed May 24, 2018.
U.S. Appl. No. 15/674,380, filed Aug. 10, 2017.

* cited by examiner

BRAIN ANEURYSM TOOL WITH A WIRE DEFLECTION MECHANISM

CROSS-REFERENCE TO RELATED APPLICATIONS

This application claims the benefit of U.S. Provisional Patent Application 62/752,825, filed Oct. 30, 2018, whose disclosure is incorporated herein by reference.

FIELD OF THE INVENTION

The present invention relates generally to medical devices, and particularly to probes for cerebrovascular applications.

BACKGROUND OF THE INVENTION

Devices, such as minimally invasive probes, were previously proposed for the treatment of brain aneurysm. For example, U.S. Pat. No. 5,980,554 describes a wire frame stent or occluding device for use within a vasculature. The device can be stretched into a double wire or single wire configuration for easy deployment into the vasculature. After the device is properly located, the distal free end will revert to its memorized hoop shape, and the strut and occluding section will revert to the memorized occluding shape. Adjustments to the position of the coil, the hoops or the struts can be made using the insertion catheter to bump and push the parts into place.

U.S. Pat. No. 9,579,104 describes intravascular implant systems and methods of positioning and detaching implants. One such system carries an implant by retaining an engagement member in a position proximal to an aperture at a distal end of the delivery system. The engagement member is retained proximal to the aperture by an elongate member that is coupled to the implant. Once the implant is in a desired implant position, the elongate member is released from the engagement member, and the implant is allowed to move away from the delivery system. In some embodiments, an assembly for deploying an implant into an aneurysm, comprises: a tubular member having (a) a member lumen in the tubular member and (b) an opening at a distal end portion of the tubular member; a coil implant configured for placement into an aneurysm and having (a) a coil; (b) a coil lumen extending longitudinally within the coil; and (c) a securing member (i) extending within the coil lumen, (ii) coupled, at a distal region of the securing member, to the coil, and (iii) having an enlarged proximal portion larger than, and positioned distal to, the opening; and an elongate member extending in the member lumen, through the opening, and coupled to the enlarged portion; wherein proximal movement of the elongate member relative to the distal end portion results in the enlarged portion contacting the distal end portion and separating from the elongate member.

U.S. Pat. No. 6,463,317 describes a method and a device for treating hemodynamically significant aneurysms especially in the intracranial and extracranial circulation regions using either X-ray fluoroscopy or real-time magnetic resonance (MR) imaging guidance. An MR-visible parachute-shaped occlusion device, e.g., containing multiple elongated filamentary loops made of a memory metal, elastomeric hydrogel or other expansible material, is deployed into the aneurysm by radial expansion of the expansible material outwardly into contact with the interior aneurysm surface. The device is firmly positioned against the interior aneurysm surface using a coating which adheres to that interior aneurysm surface. Detachment of the aneurysm occlusion device from a transport catheter is achieved by mechanical, electrical and/or chemical decoupling. The catheter systems may have attached micro-coils or may be impregnated with MR-visible agents to permit visualization in MR imaging systems.

SUMMARY OF THE INVENTION

An embodiment of the present invention provides a medical device for treating an aneurysm in a blood vessel, the medical device including a hollow shaft for insertion into the blood vessel, an exit port at a distal end of the shaft, a deflection element, and a position sensor. The hollow shaft encompasses a wire-insertion channel for leading a wire to be inserted into the aneurysm. The exit port is configured for exiting the wire from the wire-insertion channel and into the aneurysm. The deflection element is located adjacent to the exit port and configured to deflect the wire from the wire-insertion channel to the exit port. The position sensor, which is coupled to the distal end of the shaft, is configured to produce signals indicative of a position and orientation of the exit port in the blood vessel.

In some embodiments, the medical device further includes a locking mechanism, which is configured to lock the distal end in place.

There is additionally provided, in accordance with an embodiment of the present invention, a medical system for treating an aneurysm in a blood vessel, the medical system including a probe and a processor. The probe includes a hollow shaft for insertion into the blood vessel, the shaft encompassing a wire-insertion channel for leading a wire to be inserted into the aneurysm. The probe additionally includes an exit port at a distal end of the shaft, for exiting the wire from the wire-insertion channel and into the aneurysm. The probe additionally includes a deflection element, located adjacent to the exit port and configured to deflect the wire from the wire-insertion channel to the exit port. The probe further includes a position sensor, which is coupled to the distal end of the shaft and is configured to produce signals indicative of a position and orientation of the exit port in the blood vessel. The processor is configured to, based on the received signals, estimate the location and orientation of the exit port in the blood vessel relative to an opening of the aneurysm, and indicate to a user a geometrical relationship between the exit port and the opening of the aneurysm.

There is further provided, in accordance with an embodiment of the present invention, a method for treating an aneurysm in a blood vessel, the method including inserting into the blood vessel a probe. The probe includes: (a) a hollow shaft for insertion into the blood vessel, the shaft encompassing a wire-insertion channel for leading a wire to be inserted into the aneurysm, (b) an exit port at a distal end of the shaft, for exiting the wire from the wire-insertion channel and into the aneurysm, (c) a deflection element, located adjacent to the exit port and configured to deflect the wire from the wire-insertion channel to the exit port, and, (d) a position sensor, which is coupled to the distal end of the shaft and is configured to produce signals indicative of a position and orientation of the exit port in the blood vessel. Based on the received signals, the location and orientation of the exit port in the blood vessel, relative to an opening of the aneurysm, is estimated. A geometrical relationship between the exit port and the opening of the aneurysm is indicated to a user.

The present invention will be more fully understood from the following detailed description of the embodiments thereof, taken together with the drawings in which:

DETAILED DESCRIPTION OF EMBODIMENTS

Overview

Figure 1A:
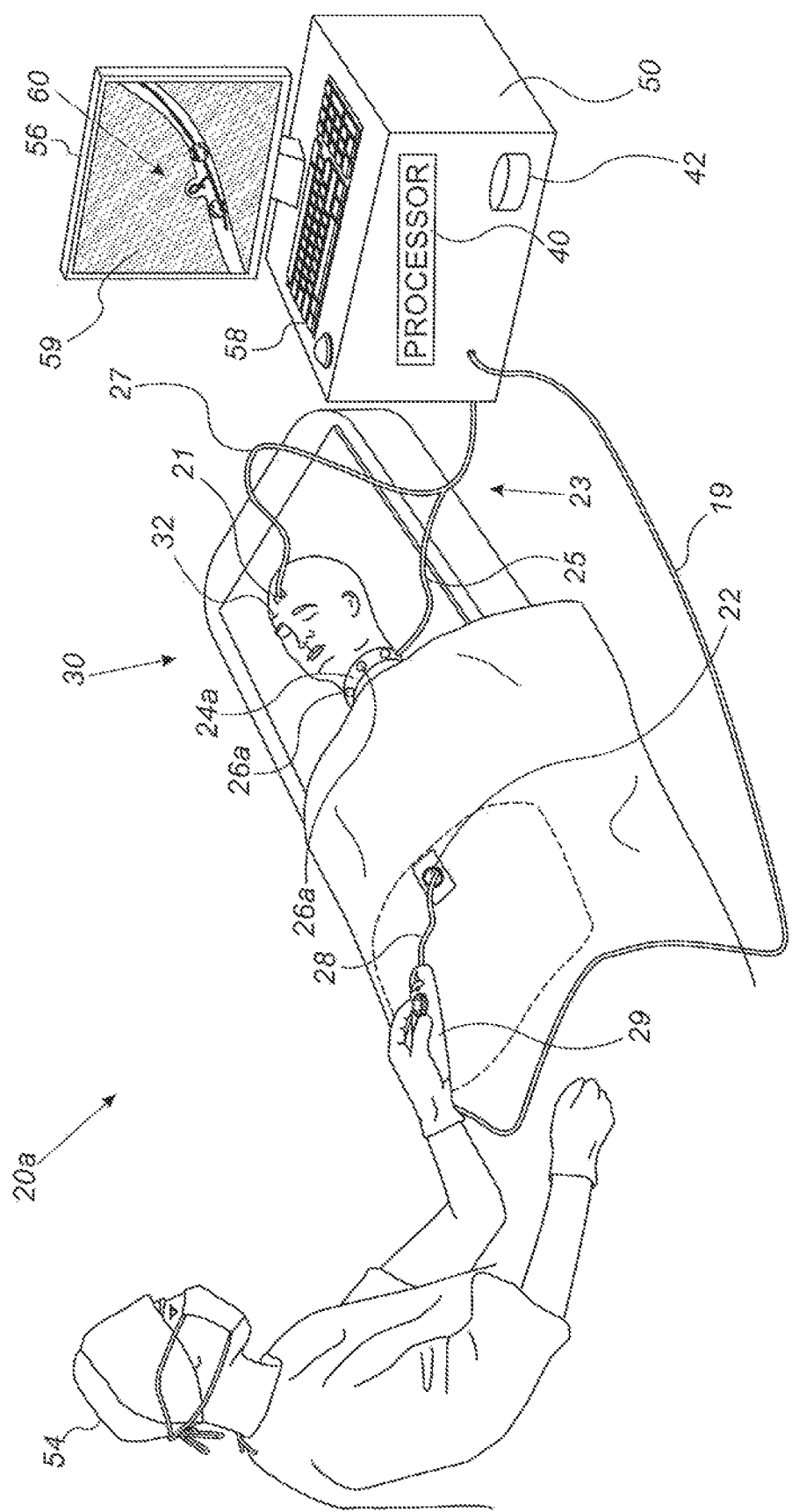
FIGS. 1A and 1B are schematic, pictorial illustrations of catheter-based cerebrovascular position tracking systems, in accordance with embodiments of the present invention.

A large brain aneurysm in a blood vessel of the brain is considered a serious medical condition. If untreated, a large aneurysm may leak or explode, causing a hemorrhagic stroke, which is a medical emergency.

The location of the aneurysm in the brain may be detected with computerized tomography (CT), fluoroscopy imaging, or magnetic resonance imaging (MRI). A physician may then insert and advance a probe, such as a catheter, to guide a very thin platinum wire, together with other materials, such as glue, into the aneurysm to form a web or mesh. However, this treatment method requires intensive fluoroscopic imaging, which exposes the patient to a high dosage of X-ray radiation, partly because the insertion process tends to be based on trial and error.

Embodiments of the present invention that are described hereinafter provide a system, a medical device (e.g., a probe), and method for treating a brain aneurism. In some embodiments, the medical device (e.g., a type of catheter), named hereinafter "brain aneurysm tool" (BAT), comprises a hollow shaft for insertion into the blood vessel, the shaft encompassing a wire-insertion channel for leading a wire to be inserted into the aneurysm. The BAT further comprises an exit port at a distal end of the shaft, for exiting the wire from the wire-insertion channel and into the aneurysm. The BAT additionally comprises a deflection element, located adjacent to the exit port and configured to deflect the wire from the wire-insertion channel to the exit port. A position sensor, which is coupled to the distal end of the shaft of the BAT is configured to produce signals indicative of a position and orientation of the exit port in the blood vessel.

Typically, the wire used is a thin platinum wire. In some embodiments, the position sensor is a magnetic location sensor which transmits position and orientation indicative signals to a catheter-based magnetic position and orientation tracking system, such as the CARTO® system (made by Biosense-Webster, Irvine, Calif.). During catheterization, the tracking system uses the indicative signals to provide the physician position and orientation of the exit port in the brain in a coordinate system of the tracking system.

The disclosed BAT also comprises one or more locks, such as inflatable balloons, which an operator can inflate in order to fix the BAT in place prior to treating the aneurysm with the wire.

In some embodiments, an aneurysm treatment system and method are provided, where, at the beginning of a catherization procedure, a processor registers the coordinate system of the tracking system with the medical images showing the aneurysm. Once registration is complete, the physician inserts the BAT into the vicinity of the aneurysm where the processor, based on indications of position and orientation provided by the magnetic sensor, adjusts the position and orientation of the distal end to bring the exit port of the BAT opposite the aneurysm opening. More generally, in an embodiment, the processor is configured to, based on the received signals, indicate to the user a geometrical relationship between the exit port and the opening of the aneurysm, such as the distance of the exit port of the BAT is from the aneurysm opening. When positioned correctly, the BAT is locked in place, for example, by inflating one or more locking balloons.

The operator then inserts the thin platinum wire into the BAT and deflects the wire directly into the aneurysm using the disclosed deflection element. In some embodiments, the insertion is assisted by a wire insertion mechanism, such as a wire insertion channel that is included in the probe, and which is configured to channel the wire along the BAT in a distal direction as the wire is being inserted distally by the physician.

Typically, the processor is programmed in software containing a particular algorithm that enables the processor to conduct each of the processor-related steps and functions outlined above.

The operator may use fluoroscopy to confirm that the wire is positioned correctly in the aneurysm and to continue the insertion. However, the overall fluoroscopic use is substantially reduced, as the trial and error aspect of wire insertion is not present in the disclosed system and method.

Thus, the disclosed tool and method for treating a brain aneurysm may simplify and by so make the clinical procedure safer, while at the same time reduce a patient's exposure to X-ray radiation.

System Description

Figure 1B:
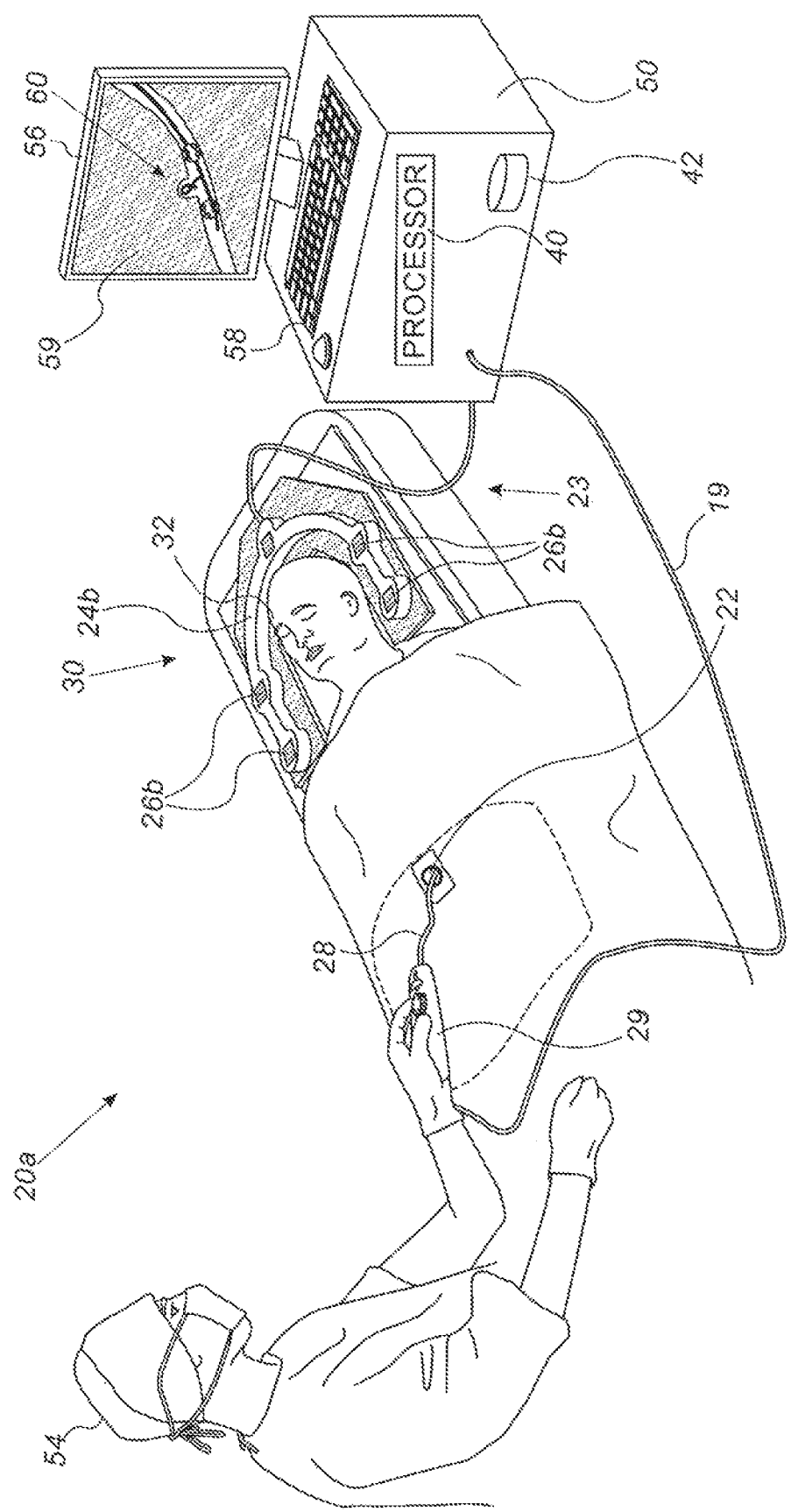

FIGS. 1A and 1B are schematic, pictorial illustrations of catheter-based cerebrovascular position tracking systems 20*a* and 20*b*, in accordance with embodiments of the present invention.

In some embodiments, prior to performing the catherization procedure, CT images of a patient 22 are acquired. The CT images are stored in a memory 42 for subsequent retrieval by a processor 40. The processor uses the images to present, for example, brain section image 59 demonstrating an aneurism 60 on a display 56. In another embodiment, during the disclosed catheterization, procedure systems 20*a* and 20*b* register a position of a distal end of a BAT 28 inside the patient's brain, with frames of reference of brain images of patient 32, herein assumed by way of example to comprise real-time fluoroscopic images that show aneurysm 60. The position of the distal end of BAT 28 is tracked using a magnetic tracking sub-system 23, which tracks position and orientation coordinates of a magnetic sensor fitted at the distal end.

Using magnetic position tracking sub-system 23, a physician 54 advances the distal end of BAT 28 through blood vessels, usually arteries, to aneurysm 60 to perform an invasive therapeutic procedure to treat aneurysm 60.

In system 20*a*, shown in FIG. 1A, a location pad 24*a*, comprised of magnetic tracking sub-system 23, is implemented as a collar around the neck of patient 32. By putting location pad 24*a* over the neck, location pad 24*a* is configured to automatically compensate for patient head movement. Location pad 24*a* comprises magnetic field radiators 26a which are fixed in position relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in U.S. Provisional Patent Application 62/675,952, filed May 24, 2018, entitled "Position Sensor on Brain Clot Sheath and Location Pad Collar," which is assigned to the assignee of the present patent application and whose disclosure is incorporated herein by reference.

Physician 54, operating system 20a, holds BAT controller handle 29, which is connected to the proximal end of BAT 28. Controller 29 allows the physician to advance and navigate BAT 28 in the brain, for example, through an entry point 22 at an artery at a thigh of patient 32. As noted above and described below, physician 54 navigates the distal end of BAT 28 using position and orientation signals from a magnetic sensor fitted at the distal end of BAT 28. Console 50 receives the position signals via a cable 19 that connects to BAT 28 via handle 29.

Elements of system 20a, including radiators 26a, are controlled by a system processor 40, comprising a processing unit communicating with one or more memories. Processor 40 may be mounted in console 50, which comprises operating controls 58 that typically include a keypad and/or a pointing device such as a mouse or trackball. Physician 54 uses operating controls on handle 29 to interact with the processor while performing the registration of system 20a. During the registration process, an image 59 of a brain section showing aneurysm 60 is presented on display 56. Subsequent to the registration process described above, physician 54 uses the operating controls to advance the distal end of BAT 28 to a location of aneurism 60 in the brain. The processor presents results of the BAT tracking procedure on display 56.

Processor 40 uses software stored in a memory 42 to operate system 20a. The software may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed steps.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be harnessed to keep it motionless. Other components of system 20b are generally identical to those of system 20a. A location tracking system using a location pad similar to location pad 24b is described in U.S. patent application Ser. No. 15/674,380, filed Aug. 10, 2017, published as U.S. Pub. No. 2019/0046272 on Feb. 14, 2019, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling additional tooling such as for drug delivery. CARTO® magnetic tracking systems, which track a location and orientation of a magnetic position sensor in an organ of a body using techniques similar to those applied by systems 20a and 20b, are produced by Biosense-Webster.

Brain Aneurysm Tool with a Wire Deflection Mechanism

Figure 2:
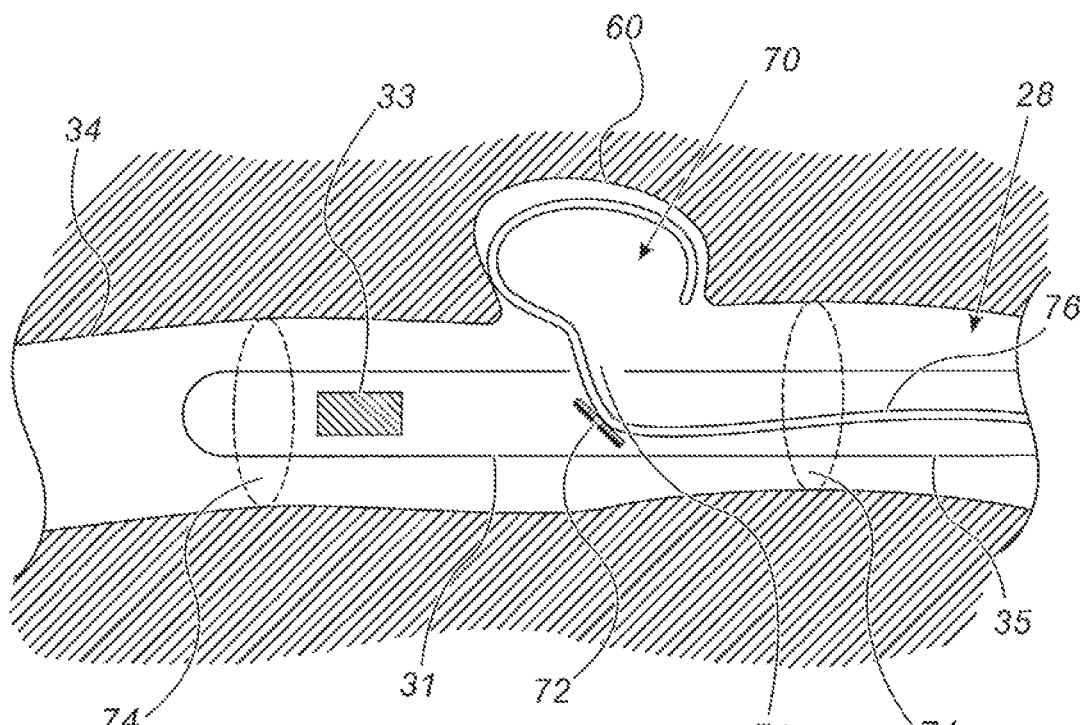
FIG. 2 is a schematic cross-sectional view of a brain aneurysm and a brain aneurysm tool (BAT) comprising a wire deflection element, in accordance with an embodiment of the present invention.

FIG. 2 is a schematic cross-sectional view of a brain aneurysm 60, and brain aneurysm tool (BAT) 28 comprising a wire deflection element 72, in accordance with an embodiment of the present invention. Typically BAT 28 has a diameter of approximately one millimeter.

As seen, aneurysm 60 bulges out of an artery 34. In some embodiments, physician 54 advances BAT 28 (e.g. a hollow shaft 35) distally in artery 34, to a location slightly beyond aneurysm 60. As seen in FIG. 2, a distal end 31 of BAT 28 comprises a magnetic position sensor 33, which is used for tracking the position and orientation of distal end 31 in the brain to navigate distal end 31 to aneurysm 60 and align distal end 31 against opening 70 of aneurysm 60, as described below.

Once approximately in place, physician 54 further adjusts the position and orientation of distal end 31 so that an exit port 71 is exactly opposite aneurysm opening 70. After being positioned correctly, locking balloons 74, inflated by physician 54, fix distal end 31 in place.

Deflection element 72, which is included in distal end 31, is configured to deflect a platinum wire 76 as it is advanced distally to exit port 71 and directly into aneurysm 60 through aneurysm opening 70.

The example illustration shown in FIG. 2 is chosen purely for the sake of conceptual clarity. In some embodiments, for example, the deflection element comprises a curved channel rather than the simple plate shape shown. In an alternative embodiment, wire 76 is made of a shape-memory alloy, such as Nitinol. In another embodiment, wire 76 is coated with a bio-compatible adherent material.

Figure 3:
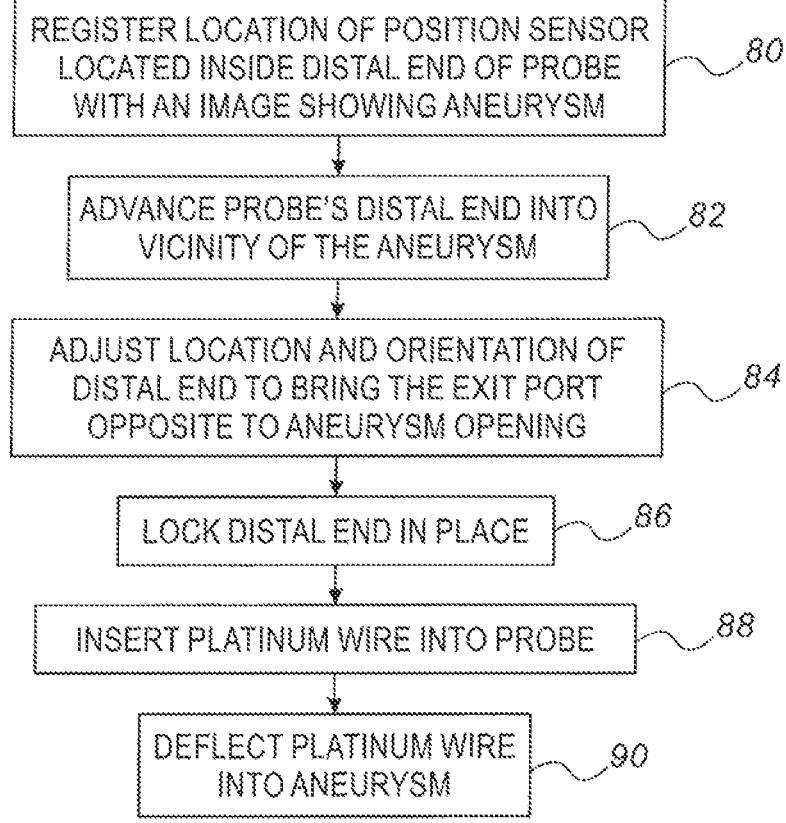
FIG. 3 is a flow chart that schematically illustrates a method for treatment of a brain aneurysm, in accordance with an embodiment of the present invention.

FIG. 3 is a flow chart that schematically illustrates a method for treatment of a brain aneurysm, in accordance with an embodiment of the present invention. The process begins with physician 54 registering the coordinate system of the catheter-based magnetic tracking system with the coordinate system of medical images that show aneurysm 60, at a registration step 80. Next, physician 54 advances distal end 31 of BAT 28 into the vicinity of aneurysm 60, at a BAT advancement step 82.

Next, using the spatial information obtained by the dedicated algorithm, physician 54 adjusts the location and orientation of distal end 31 so as to bring exit port 71 opposite to opening 70 of aneurysm 60, at a distal end adjustment step 84. Next, physician 54 locks the distal end in place, for example by inflating locking balloons 74, at a distal end locking step 86. Next, physician 54 inserts platinum wire 76 into BAT 28, at a wire insertion step 88. Finally, physician 54 deflects platinum wire 76 using deflection element 72 as wire 76 is further inserted distally, at an aneurysm treatment step 90.

The example flow chart shown in FIG. 3 is chosen purely for the sake of conceptual clarity. In additional embodiments, for example, physician 54 fills aneurysm 60 with a polymeric mesh. In some embodiments, steps 80-86 can be carried out without fluoroscopy, by physician 54 using previously acquired medical images of the clot, such as CT images.

Although the embodiments described herein mainly address cerebrovascular applications, the methods and systems described herein can also be used in other applications, such as in treating aneurysms in a sufficiently large blood vessel at any location of in the body that can accommodate the disclosed tool.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical device for treating an aneurysm in a blood vessel, the medical device comprising:
   a hollow shaft for insertion into the blood vessel, the shaft encompassing a wire-insertion channel for leading a wire to be inserted into the aneurysm;
   an exit port at a distal end of the shaft, for exiting the wire from the wire-insertion channel and into the aneurysm;
   a deflection element, located within the wire-insertion channel and adjacent to the exit port and configured to deflect the wire from the wire-insertion channel to the exit port; and
   a position sensor, which is coupled to the distal end of the shaft and is configured to produce signals indicative of a position and orientation of the exit port in the blood vessel.

2. The medical device according to claim 1, and comprising a locking mechanism, which is configured to lock the distal end in place.

3. The medical device according to claim 2, the locking mechanism including at least one locking balloon.

4. The medical device according to claim 3, the at least one locking balloon comprising a first locking balloon and a second locking balloon.

5. The medical device according to claim 4, the exit port being longitudinally interposed between the first locking balloon and the second locking balloon.

6. The medical device according to claim 1, the exit port comprising a laterally oriented opening formed through a sidewall of the shaft.

7. The medical device according to claim 6, the distal end of the shaft having a closed configuration, the exit port being positioned proximal to the closed distal end of the shaft.

8. The medical device according to claim 6, the deflection element including a surface obliquely oriented relative to a longitudinal axis of the shaft.

9. The medical device according to claim 6, the deflection element including a curved region at a distal end of the wire-insertion channel.

10. The medical device according to claim 6, the deflection element being laterally positioned in relation to the exit port.

11. The medical device according to claim 1, the position sensor being longitudinally positioned between the exit port and the distal end of the shaft.

12. The medical device according to claim 1, the position sensor longitudinally positioned between the deflection element and the distal end of the shaft.

13. A medical system for treating an aneurysm in a blood vessel, the medical system comprising:
   a probe, comprising:
   a hollow shaft for insertion into the blood vessel, the shaft encompassing a wire-insertion channel for leading a wire to be inserted into the aneurysm;
   an exit port at a distal end of the shaft, for exiting the wire from the wire-insertion channel and into the aneurysm;
   a deflection element, located within the wire-insertion channel and adjacent to the exit port and configured to deflect the wire from the wire-insertion channel to the exit port; and
   a position sensor, which is coupled to the distal end of the shaft and is configured to produce signals indicative of a position and orientation of the exit port in the blood vessel; and
   a processor, which is configured to:
      based on the received signals, estimate the location and orientation of the exit port in the blood vessel relative to an opening of the aneurysm; and
      indicate to a user a geometrical relationship between the exit port and the opening of the aneurysm.

14. A method for treating an aneurysm in a blood vessel, the method comprising:
   inserting into the blood vessel a probe comprising:
      a hollow shaft for insertion into the blood vessel, the shaft encompassing a wire-insertion channel for leading a wire to be inserted into the aneurysm;
      an exit port at a distal end of the shaft, for exiting the wire from the wire-insertion channel and into the aneurysm;
      a deflection element, located within the wire-insertion channel and adjacent to the exit port and configured to deflect the wire from the wire-insertion channel to the exit port; and
      a position sensor, which is coupled to the distal end of the shaft and is configured to produce signals indicative of a position and orientation of the exit port in the blood vessel;
   based on the received signals, estimating the location and orientation of the exit port in the blood vessel relative to an opening of the aneurysm; and
   indicating to a user a geometrical relationship between the exit port and the opening of the aneurysm.

15. The method according to claim 14, and comprising locking the distal end in place using a locking mechanism.

16. The medical device according to claim 15, the locking mechanism including one or more balloons, the locking the distal end in place including inflating the one or more balloons.

17. The method according to claim 14, wherein indicating to a user a geometrical relationship comprises indicating when the exit port of the probe is opposite the opening of the aneurysm.

18. The method according to claim 14, and comprising inserting a wire in a distal direction through the wire-insertion channel and deflecting the distally inserted wire through the exit port using the deflection element.

19. The method according to claim 18, further comprising:
   advancing the probe into the blood vessel to a position where the distal end of the shaft is positioned distally in relation to the aneurysm and the exit port is positioned laterally adjacent to the aneurysm; and
   advancing a distal portion of the wire out through the exit port and into the aneurysm.

20. The method according to claim 14, the aneurysm being located in a brain of a patient.

* * * * *